US012385917B2

(12) United States Patent
Kinney et al.

(10) Patent No.: US 12,385,917 B2
(45) Date of Patent: Aug. 12, 2025

(54) METHODS AND COMPOSITIONS FOR TRACKING VEGETATION

(71) Applicant: Colorado State University Research Foundation, Fort Collins, CO (US)

(72) Inventors: Chad A. Kinney, Pueblo, CO (US); James Carsella, Pueblo West, CO (US); Brian Vanden Heuvel, Colorado Springs, CO (US); David Boston, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 1194 days.

(21) Appl. No.: 17/049,958

(22) PCT Filed: Apr. 26, 2019

(86) PCT No.: PCT/US2019/029332
§ 371 (c)(1),
(2) Date: Oct. 22, 2020

(87) PCT Pub. No.: WO2019/210154
PCT Pub. Date: Oct. 31, 2019

(65) Prior Publication Data
US 2021/0231658 A1    Jul. 29, 2021

Related U.S. Application Data

(60) Provisional application No. 62/663,098, filed on Apr. 26, 2018.

(51) Int. Cl.
*G01N 33/569* (2006.01)
*G01N 33/58* (2006.01)
*G01N 33/68* (2006.01)

(52) U.S. Cl.
CPC ..... *G01N 33/56961* (2013.01); *G01N 33/581* (2013.01); *G01N 33/582* (2013.01); *G01N 33/6848* (2013.01)

(58) Field of Classification Search
None
See application file for complete search history.

(56) References Cited

U.S. PATENT DOCUMENTS

2006/0178501 A1    8/2006    Summers et al.

OTHER PUBLICATIONS

Allen et al. Progress in Lipid Research (2015)58:97-120.*
Bauer, R., Rupe, C. O. Use of Syringaldazine in a Photometric Method for Estimating "Free" Chlorine in Water. Anal. Chem. 1971, 43 (3), 421-425.
Cheng, C. M., Martinez, A. W., Gong, J., Mace, C. R., Phillips, S. T., Carrilho, E., Mirka, K. A., Whitesides, G. M. Paper-Based Elisa. Angew. Chemie—Int. Ed. 2010, 49 (28), 4771-4774.
Majcherczyk, A., Johannes, C., Huttermann, A. Oxidation of Aromatic Alcohols by Laccase from Trametes Versicolor Mediated by the 2,2'-Azino-Bis-(3-Ethylbenzothiazoline-6-Sulphonic Acid) Cation Radical and Dication. Appl. Microbiol. Biotechnol. 1999, 51 (2), 267-276.
Hapiot, P., Pinson, J., Neta, P., Rolando, C. Electrochemical Behaviour of Syringaldazine, a Colorimetric Redox Reagent. J. Electroanal. Chem. 1993, 353 (1-2), 225-235.
Gurung, P., Uptake of Human Pharmaceuticals in Plants Grown Under Hydroponic Conditions. A Master's Thesis Presented to the Faculty of the College of Science and Y Mathematics. Master of Science in Applied Natural Science—Chemical Science Emphasis. Colorado State University—Pueblo. Pueblo, CO. May 2009; p. I, Abstract; p. 1. Introduction section; p. 11, First Paragraph; p. 15, Materials and Methods section; p. 20, Table 5; p. 20.Results and Discussion section, Second Paragraph; p. 24, Conclusion section to p. 25, First Paragraph.
Haddix, M, et al., Dual, Differential Isotope Labeling Shows the Preferential Movement of Labile Plant Constituents into Mineral-Bonded Soil Organic Matter. Global Change Biology. Jan. 3, 2016, vol. 22; pp. 2301-2312. DOI:10.1111/gcb.13237; Abstract; p. 2305, Left Column.
Lisowski, P, et al., Microfluidic Paper-Based Analytical Devices (microPADs) and Micro Total Analysis Systems (micro-TAS): Development, Applications and Future Trends. Chromatographia. Feb. 22, 2013, vol. 76: pp. 1201-1214. DOI: 10.1007/s10337-013-2413-y; Abstract; p. 1202, Left Column.
Chalk, PM. From Production to Consumption: Tracing C, N, and S Dynamics in Brazilian Agroecosystems Using Stable Isotopes. Pesq. agropec. bras., Brasilia, 2016, vol. 51, No. 9; pp. 1039-1050. DOI: 10.1590/50100-204X2016000900003; Abstract; p. 1044, Left col. Third Paragraph; p. 1045, Geographic origin section, First Paragraph; p. 1045, Right col. Fourth Paragraph.
Yu, S, et al. Testing the Efficiency of Plant Artificial microRNAs by Transient Expression in Nicotiana benthamiana Reveals Additional Action at the Translational Level. Frontiers in Plant Science. Nov. 19, 2014, vol. 5, Article 622. D01: 10.3389/fpls.2014.00622; Abstract.
International Search Report and Written Opinion regarding PCT/US2019/029332, dated Jul. 10, 2019.

* cited by examiner

*Primary Examiner* — Medina A Ibrahim
(74) *Attorney, Agent, or Firm* — Dentons US LLP

(57) ABSTRACT

The present disclosure provides compositions and methods for tracking vegetation through the production and distribution cycle, and for distinguishing between plants or crops having different characteristics.

32 Claims, 11 Drawing Sheets

| m/z | Ion | $^{15}N$ | $^{15}N$ | $^{13}C$-methyl | $^{13}C$-carbonyl | $^{13}C$-ring | $^{13}C$-methyl, $^{15}N$ | $^{13}C$-carbonyl, $^{15}N$ | $^{13}C$-ring, $^{15}N$ |
|---|---|---|---|---|---|---|---|---|---|
| 153.06 | | | | 154.06 | 154.06 | 159.07 | | | |
| 125.1 | | | | 126.06 | 125.1 | 131.08 | | | |
| 93.2 | | | | 93.2 | 93.2 | 100.06 | | | |
| 301.21 | | 303.11 | 301.21 | 303.12 | 303.12 | 313.16 | 305.12 | 305.12 | 315.15 |
| 177.05 | | 179.06 | 177.05 | 178.07 | 180.08 | 183.09 | 180.06 | 181.07 | 185.08 |
| 153.09 | | 153.07 | 153.09 | 153.07 | 153.07 | 158.09 | 154.07 | 154.07 | 159.09 |
| 150.08 | | 151.05 | 150.08 | 151.06 | 151.08 | 156.08 | 152.08 | 152.06 | 157.07 |
| 125.12 | | 125.12 | 125.12 | 126.06 | 125.12 | 131.08 | 126.06 | 125.06 | 131.08 |
| 123.08 | | 123.04 | 123.08 | 124.05 | 123.04 | 129.06 | 124.05 | 123.04 | 129.08 |
| 361.14 | | 361.13 | 361.14 | 365.15 | 363.15 | 373.18 | 367.15 | 365.14 | 375.17 |
| 207.07 | | 209.07 | 207.07 | 209.08 | 210.08 | 213.1 | 211.08 | 211.08 | 215.09 |

FIG. 8

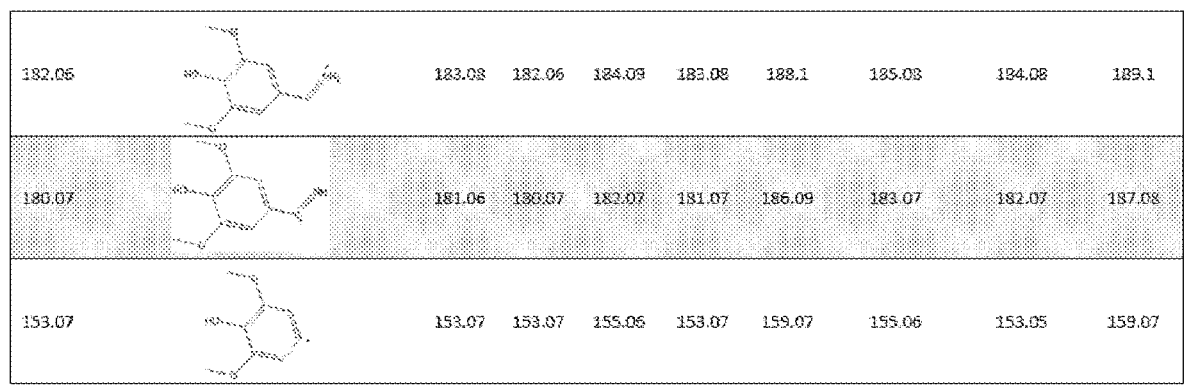
FIG. 8 (con't)

METHODS AND COMPOSITIONS FOR TRACKING VEGETATION

CROSS REFERENCE TO RELATED APPLICATIONS

This application is a 371 National Stage application of International Application No. PCT/US2019/029332, filed Apr. 26, 2019, which claims the benefit of U.S. Provisional Application 62/663,098, filed Apr. 26, 2018, each of which is incorporated herein by reference in its entirety.

FIELD OF THE INVENTION

The present disclosure relates to the field of biotechnology. More specifically, the disclosure relates to compositions and methods for tracking vegetation through the production and distribution cycle, and for distinguishing between plants or crops having different characteristics.

BACKGROUND

Certain industries require a reliable test to determine where a substance, food product, or certain vegetation originated. Food vendors, such grocery stores, mark "organic" on certain products which meet a required standard. The cannabis industry has standards for their products, be it medical, recreational, organic, or otherwise. A problem that faces these industries is how to know for certain that the product they receive has originated from the correct farm or production facility. Traceability, transparency, and authenticity are the concerns that need to be met. Current art utilizes eTracking by furnishing the farmer or the like with technology to upload the harvest or animal information to a server. The farmer is then provided with a unique serial number and/or bar code for that good, usually in the form of a sticker. That information will then be passed on to everyone in the supply chain until it is purchased by the consumer.

The problem with the current state-of-the-art is that it can be too easily tampered with. Somewhere along the line, the information, be it on a sticker or otherwise, can be switched, altered, or removed.

Therefore there is a need in the industry to have a more reliable tracking methods and compositions for these products.

SUMMARY OF THE INVENTION

The present disclosure provides a method for identifying the source of a plant or part thereof, comprising contacting the plant or a part thereof with a first compound indicative of source and capable of being detected by a field-based assay, the compound comprising at least a first stable isotope label at a first location in the compound, and identifying the source of the plant or a part thereof by detecting the compound, the absorption characteristics of the compound, or the location of the first stable isotope label in the compound. In some embodiments the compound comprises at least a first stable isotope label at a first location in the compound, and the source of the plant or a part thereof is identified by detecting the location of the first stable isotope label in the compound. In certain embodiments, the source of the plant is identified using the field-based assay or test to detect the compound and/or amount of the compound. In other embodiments, the source of the plant is identified using a light- or spectral-based assay or test to determine the absorption characteristics of the compound. In yet other embodiments, the source of the plant is identified using a laboratory-based assay or test to determine the presence and/or location of the first stable isotope label, and/or the amount of the first stable isotope label, in the compound. In further embodiments, the source of the plant is identified using a combination of the field-based assay and the light-based assay, the field-based assay and the laboratory-based assay, the light-based assay and the laboratory-based assay, or the field-based assay, the light-based assay and the laboratory-based assay.

In some embodiments, the method further comprises contacting a plurality of plants or parts thereof with said first compound and at least a second compound, wherein the first compound is distinguishable from the second compound using said field test. In other embodiments the first and second compounds comprise at least a first stable isotope label at a first location in the first and second compounds and wherein the first compound is distinguishable from the second compound using said field test. In particular embodiment the first compound is indicative of a first source for the plant or part thereof and the second compound is indicative of a second source for the plant or part thereof. In additional embodiments, the method further comprises contacting the plurality of plants with a plurality of isotopic labeled variants of said first compound or said second compound comprising stable isotope labels in different locations or different isotope labels, wherein the variants are capable of serving as an indicator of source. In various embodiments, the particular isotope label used in the first and/or second compound, the combination of different isotope labels used in the first and/or second compound, or the specific locations of the isotope labels or different isotope labels used in the first and/or second compound are indicative of the source of the plants or parts thereof. In some embodiments, the variants comprise a first and second different stable isotope label or a single stable isotope label at a plurality of locations in the compound.

In certain embodiments, the first compound is applied to the surface of the plant or part thereof. For example the plant or part thereof can be contacted with a solution comprising the first compound, such as by spraying and the like, or the plant or part thereof can be soaked, doused or washed with a solution comprising the first compound. In some embodiments, the solution comprising the first compound is aqueous-based, while in other embodiments the first compound is comprised in an organic-based solvent or solution. In additional embodiments, the first compound can be applied to the surface of the plant or part thereof at an early stage of the life-cycle of the plant, for example after the plant has emerged from its seed and has been growing for about 1 week, about 2 weeks, about 3 weeks, about 4 weeks, about 5 weeks, about 6 weeks, about 7 weeks, about 8 weeks, about 9 weeks, about 10 weeks, about 11 weeks or about 12 weeks or more. In other embodiments, the first compound is applied to the plant or part thereof at a later stage of the life-cycle of the plant, even up to the point when the plant or part thereof is harvested. In particular embodiments, the first compound is applied to the plant or part thereof after the plant or part thereof has been harvested.

In some embodiments, the first compound is a pharmaceutical compound, a nutraceutical compound, a small molecule (small organic molecule) or a vitamin. In certain embodiments, the first compound is carbamazepine, vanillin azine, vanillin, syringaldazine or a terpene. In other embodiments, the first compound is a protein, enzyme or peptide. In particular embodiments, the peptide is between about 5 amino acids and about 20 amino acids in length, between about 8 amino acids and about 16 amino acids in length, or between about 10 amino acids and about 15 amino acids in length. Thus, in certain embodiments, the peptide is about 5, about 6, about 7, about 8, about 9, about 10, about 11, about 12, about 13, about 14, about 15, about 16, about 17, about 18, about 19 or about 20 amino acids in length. In additional embodiments, one or more of the amino acids in the protein, enzyme or peptide is a modified amino acid.

In further embodiments, the first compound is a sugar (saccharide) or a polysaccharide. In some embodiments, the polysaccharide is between about 2 sugars and about 20 sugars in length, between about 3 sugars and about 18 sugars in length, or between about 5 sugars and about 15 sugars in length. Thus, in particular embodiments, the polysaccharide is about 2, about 3, about 4, about 5, about 6, about 7, about 8, about 9, about 10, about 11, about 12, about 13, about 14, about 15, about 16, about 17, about 18, about 19 or about 20 sugars in length. In some embodiments, the polysaccharide is comprised of a single sugar, while in other embodiments the polysaccharide is comprised of two or more different sugars. In further embodiments, the sugar, or one or more of the sugars in the polysaccharide, is a modified sugar.

In yet other embodiments, the first compound is a nucleic acid molecule. In particular embodiments, the nucleic acid molecule is between about 10 nucleotides and about 30 nucleotides in length, between about 15 nucleotides and about 25 nucleotides in length, or between about 18 amino acids and about 22 nucleotides in length. Thus, in some embodiments, the nucleic acid molecule is about 10, about 11, about 12, about 13, about 14, about 15, about 16, about 17, about 18, about 19, about 20, about 21, about 22, about 23, about 24, about 25, about 26, about 27, about 28, about 29 or about 30 nucleotides in length. In certain embodiments, one or more of the nucleotides in the nucleic acid molecule is a modified nucleotide.

In certain embodiments, the field-based assay or test is a quick or rapid test that can be performed within 90 minutes, within 60 minutes, within 45 minutes, within 30 minutes, within 15 minutes, within 10 minutes, or within 5 minutes or less from the time the assay is initiated, for example, from when at least a portion of the compound being assayed is removed from the plant or part thereof for analysis, or the plant or part thereof is contacted to detect the compound. In some embodiments, the field-based assay is a color-based assay that measures the appearance or disappearance of color, while in other embodiments the field-based assay is a fluorescence-based assay that measures the appearance or quenching or fluorescence. In one embodiment the field-based assay is an immunological assay that utilizes an antibody, or fragment of an antibody, that binds specifically or preferentially to the first compound. In another embodiment the field-based assay is a protein or enzyme-based assay where the protein or enzyme reacts with an indicator molecule to produce a color-based or fluorescence-based change, In an embodiment wherein the first compound is a nucleic acid molecule the field-based assay can be a nucleic acid binding assay that utilizes a short (10-30 nucleotides in length) nucleic acid probe that binds specifically or preferentially to the first compound, although in certain embodiments an immunological assay can be used wherein the first compound is a nucleic acid molecule.

In certain embodiments, the first stable isotope label is independently selected from the group consisting of $^2$H, $^{13}$C, $^{15}$N, $^{17}$O, $^{18}$O, $^{19}$F, $^{31}$P, $^{33}$S, $^{34}$S, $^{36}$S or $^{37}$Cl. In some embodiments, the location or quantity of the first stable isotope label, and the second stable isotope label when present, in the compound is identified by a laboratory-based assay or test. In particular embodiments, the laboratory-based assay or test is conducted on a sample of the plant or part thereof, or a sample comprising the first compound that was removed from the plant or part thereof, that is sent to a facility off-site to perform the analysis. Therefore in certain embodiments, laboratory-based tests or assays take at least a day, and in some embodiments up to a week or more, to obtain the desired results. In some embodiments, the laboratory-based test or assay is mass spectrometry, gas chromatography-mass spectrometry (GC/MS), liquid chromatography-quadrupole time-of flight (LC/QToF) or a mass spectrometry-based assay, such as matrix assisted laser desorption/ionization-time of flight (MALDI-TOF) mass spectrometry, tandem mass spectrometry, liquid chromatography-mass spectrometry, or liquid chromatography-tandem mass spectrometry. In further embodiments, the plant or part thereof is identified by a field-based assay and/or a light-based assay and/or a laboratory-based assay.

In some embodiments, at least a portion of the first compound is removed from the plant or part thereof before the identifying step, for example by desorbing at least a portion of the first compound from the plant or part thereof with water, before the compound is identified. In other embodiments, a portion of the plant or part thereof, for example a portion of a leaf of the plant, is removed for analysis. In various embodiments, the plant part is a cell, a seed, a root, a stem, a leaf, a head, a flower, or pollen.

In further embodiments, the first compound is indicative of the intended use of or the producer of the plant or part thereof, or the conditions under which the plant or part thereof was grown (for example conditions certified to be "organic"). In other embodiments, the location of the first stable isotope label and the second stable isotope label in the compound, the quantity of stable isotope labels in the compound, or the variants of isotope labeled forms of the compound is indicative of the origin of the plant or part thereof, or the intended use of or the producer of the plant or part thereof, or the conditions under which the plant or part thereof was grown (for example conditions certified to be "organic").

The present disclosure also provides a method of distinguishing a first plant or part thereof from a second plant or part thereof, comprising obtaining a plant or part thereof that has been contacted with a first compound capable of being detected by a field-based assay or a second compound capable of being detected by a field-based assay, and detecting in a sample of the plant or part thereof the first compound or the absorption characteristics of the first compound, or the second compound or the absorption characteristics of the second compound, wherein the presence of the first compound is indicative of the sample comprising the first plant or part thereof and the presence of the second compound is indicative of the sample comprising the second plant or part thereof. In some embodiments the first compound comprises a first stable isotope label at a first location in the first compound and a second stable isotope label at a second location in the first compound, the second compound comprises a third stable isotope label at a first location in the second compound and a fourth stable isotope label at a second location in the second compound, and detecting in a sample of the plant or part thereof the location of the first stable isotope label and the second stable isotope label in the first compound, or the second compound, or the location of the third stable isotope label and the fourth stable isotope label in the second compound, wherein the presence of the first compound is indicative of the sample comprising the first plant or part thereof and the presence of the second compound is indicative of the sample comprising the second plant or part thereof.

In certain embodiments, the first compound and the second compound are different compounds, while in other embodiments the first compound and the second compound are the same compound that differ only in the presence of different stable isotope labels, or have the same stable isotope label in different locations within the compound. Thus in one embodiment the first compound is carbamazepine, vanillin azine, vanillin, syringaldazine or a terpene comprising a first stable isotope label at a first position and a second stable isotope label at a second position, and the second compound is carbamazepine, vanillin azine, vanillin, syringaldazine or a terpene comprising the first stable isotope label at a third position and the second stable isotope label at a fourth position, while in another embodiment the first compound is carbamazepine, vanillin azine, vanillin, syringaldazine or a terpene comprising a first stable isotope label at a first position and a second stable isotope label at a second position, and the second compound is carbamazepine, vanillin azine, vanillin, syringaldazine or a terpene comprising a third stable isotope label at the first position and a fourth stable isotope label at the second position.

The first plant and the second plant can be distinguished for a variety of reasons, including, but not limited to, different intended uses of the first and second plants, different growth conditions of the first and second plants, different sources of the first and second plants, or different growers or producers of the first and second plants. In one embodiment the first plant is medical cannabis and the second plant is recreational cannabis. In another embodiment the first plant is an organic product and the second plant is a non-organic product. In yet another embodiment the first plant is grown without the use of herbicides and the second plant is grown in the presence of herbicides. In still another embodiment the first plant is from a first location (for example a particular farm, area, state or country) and the second plant is from a second location. In a further embodiment the first plant is from a first grower and the second plant is from a second grower. In some embodiments, at least a portion of the first compound or the second compound is removed from the plant or part thereof, for example by desorbing with water, before the identifying step. In other embodiments, a portion of the first and/or second plant or part thereof, for example a portion of a leaf of the first and/or second plant, is removed before the identifying step. The variety of different compounds that can be used, the variety of different stable isotope labels that can be used, and the variety of different locations within any given compound for the stable isotope labels, means that an extremely large number of different variations can be produced to distinguish any number of different characteristics of one or more plants or parts thereof.

The present disclosure additionally provides a composition comprising a first plant or part thereof comprising a first compound capable of being detected by a field-based assay and a second plant or part thereof comprising a second compound capable of being detected by a field-based assay. In some embodiments the first compound comprises a plurality of stable isotope labels at a plurality of locations in the first compound, and the second compound comprises a plurality of stable isotope labels at a plurality of locations in the second compound. In certain embodiments, the first compound is distinguishable from the second compound by being different compounds. In other embodiments, the plurality of stable isotope labels at a plurality of locations in the first compound are distinguishable from the plurality of stable isotope labels at a plurality of locations in the second compound by a laboratory-based assay.

The present disclosure further provides a composition comprising a compound capable of being detected by a field-based assay, the compound comprising a first stable isotope label at a first location in the compound and a second stable isotope label at a second location in the compound.

BRIEF DESCRIPTION OF THE DRAWINGS

For a more complete understanding of the features and advantages of the present disclosure, reference is now made to the detailed description of the disclosure along with the accompanying figures. The drawings described herein are for illustration purposes only and are not intended to limit the scope of the present teachings in any way.

FIG. 8: Fragments created by MSMS-collision with ionized argon in quad 2 of the MSMS.

DETAILED DESCRIPTION

Figure 1:
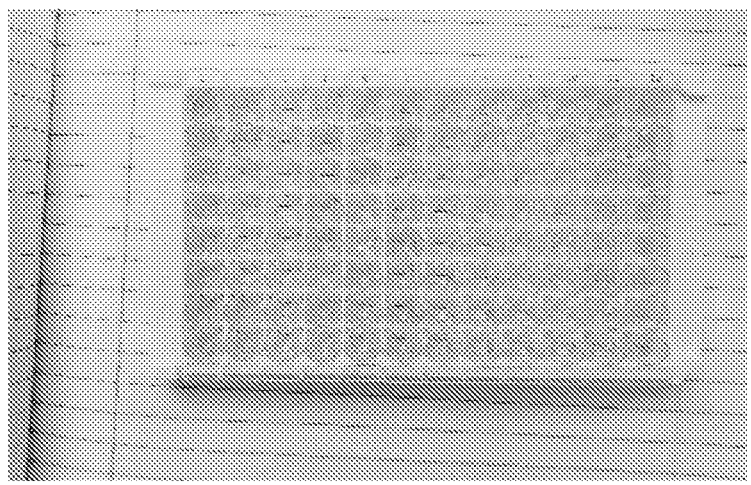
FIG. 1: Elisa antibody test for the presence of carbamazepine in the hemp wash solution. The presence of a dark yellow color corresponds to no carbamazepine. The greater the quantity of carbamazepine the less of the yellow color is present.

To overcome the shortcomings of the current state-of-the-art tracking approaches, the present approach was developed to use a molecular tag or chemical barcode added to the surface of vegetation intended for sale/consumption to differentiate between types of product, be it organic/non-organic or, for the cannabis industry, medical marijuana/recreational marijuana/hemp, or to verify the origin or grower, or any other distinguishing features of the vegetation. Three different techniques with differing complexities and precisions to identify the product can be utilized with this method: (1) a quick field-based test to determine basic information on the compound; (2) a light- or spectral-based detection technique to determine more specific information on the compound; and (3) a laboratory-based test that uses mass spectrometry to ensure complete accuracy and to determine all of the available information on stable isotope-labeled compounds.

A. Compounds

A wide variety of chemical compounds are suitable for use in the present disclosure. In general, such compounds can fall into a number of different classes, including, but not limited to, organic compounds, including, but not limited to, pharmaceutical compounds, nutraceutical compounds, small molecules, sugars, polysaccharides, vitamins, peptides, proteins, enzymes, and nucleic acids. The term "small molecule," as used herein, generally refers to an organic compound either synthesized in the laboratory or found in nature, that has a molecular weight of less than about 2500 Daltons, for example terpenes. Examples of such small molecules can be found in U.S. Pat. No. 7,109,377, which is incorporated herein by reference in its entirety. The term "polysaccharide," as used herein, refers to a polymer of sugars that contains at least two sugar residues. A polysaccharide may include natural sugars (e.g., glucose, fructose, galactose, mannose, arabinose, ribose and xylose) and/or modified sugars (e.g., 2'-deoxyribose), and can include a single type of sugar, or two or more different sugars. Any compound that can be labeled with a plurality of different stable isotopes and can be identified by one or more of the field-based tests or assays as described below is contemplated for use in the present disclosure.

B. Stable Isotopes

The compounds of the present disclosure can be labeled with a plurality of stable, or heavy, isotopes. In general stable isotopes have a different (e.g., greater) mass than the "normal" isotope with the greatest natural abundance. For example the "normal" isotope of carbon is $^{12}C$, whereas $^{13}C$ is a stable isotope of carbon that has one additional neutron, and therefore has a greater mass than $^{12}C$. Mass spectrometry assays, such as those described herein, can distinguish between compounds that are labeled with one or more stable isotopes from the same compound that does not include such stable isotopes, due to the difference in mass between the two compounds, or in certain aspects can distinguish between compounds that are labeled at different locations in the compound. Methods and reagents for isotope labeling of compounds are well-known to those of skill in the art. For example, in some embodiments polymeric molecules are generated from monomers, such as sugars, amino acids or nucleotides, at least some of which are labeled with a plurality of stable isotopes.

A large number of stable isotopes are known to those of skill in the art, and are contemplated for use in the present disclosure. Such stable isotopes include, but are not limited to, $^2H$ (or deuterium), $^{13}C$, $^{15}N$, $^{17}O$, $^{18}O$, $^{19}F$, $^{31}P$, $^{33}S$, $^{34}S$, $^{36}S$ and $^{37}Cl$.

C. Field-Based Tests or Assays

"Field-based tests" or "field-based assays," as used herein, means tests or assays that are generally rapid and easy to perform with equipment that can be used on vegetation or seeds post-harvest to be analyzed, or that can be conducted on-site without the need to send samples to a different location for analysis. Often, such field-based tests are color-based (the appearance or disappearance of color, including black or white) or fluorescence-based (for example the quenching of fluorescence) tests that fall into three major classes, immunological-based (or protein-based), enzyme based and nucleic-acid based tests. Field-based tests generally provide a limited amount of information, for example the presence or identity of a specific compound, or in some cases the amount of the compound.

Immunological-based tests utilize one or more immunological agents (for example an antibody or a fragment of an antibody that can still bind to the compound) that are specific (bind specifically to) for the compound to be analyzed or detected, and that generally produce color when bound to the compound, reduce color when bound to the compound, increase fluorescence when bound to the compound, or quench fluorescence when bound to the compound. In certain embodiments, a protein-based test, such as avidin or streptavidin binding to biotin (as the compound to be analyzed), or an enzyme bound to avidin or streptavidin (such as a phosphatase) that reacts with an indicator molecule to cause a color change, can be utilized.

Nucleic-acid based tests are used to analyze nucleic acid-based compounds, and like the immunological-based tests are specific for the nucleic acid-based compound to be analyzed or detected, and generally produce color when bound to the compound, reduce color when bound to the compound, increase fluorescence when bound to the compound, or quench fluorescence when bound to the compound.

D. Laboratory Based Tests or Assays

"Laboratory-based tests" or "laboratory-based assays," as used herein means tests or assays that are more complex and time-consuming than field-based tests or assays, and generally involve removing a sample from the plant or part thereof (for example a sample of compound desorbed from the plant or part thereof with water) that is send or shipped to an off-site facility (distinct from the field in which the vegetation to be tested is growing) for analysis. Laboratory-based tests or assays generally involve the use of sensitive and complex instruments that are not conducive for moving to or use in the field in which the vegetation to be tested is growing.

In general the laboratory-based tests or assays for use in the present disclosure are mass spectrometry-based analyses, including, but not limited to, mass spectrometry, matrix assisted laser desorption/ionization-time of flight (MALDI-TOF) mass spectrometry, tandem mass spectrometry, liquid chromatography-mass spectrometry, liquid chromatography-tandem mass spectrometry analyses, liquid chromatography-quadrupole time of flight (LC/QTOF), or gas chromatography-mass spectrometry. Such tests or assays provide very detailed information about the compound to be analyzed, such as the presence and/or location of stable isotope labels. Mass spectrometry analyses are very sensitive, and can distinguish between compounds that differ in mass due to the presence or absence of one or more stable isotopes in the compound. Such mass spectrometry assays are well-known to those of skill in the art.

EXAMPLES

The following examples are included to demonstrate preferred embodiments of the present disclosure. It should be appreciated by those of skill in the art that the techniques disclosed in the examples, which follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the present disclosure.

Example 1: Detection of Compound by Antibody

In the present exemplary embodiment, a farmer or regulatory agent will spray, or adhere in some way, a custom mixture isotope labeled compound onto their product. In this example the compound will have a corresponding antibody that is specific to that compound. That antibody (typically in solution) can then be combined with the compound to determine whether there is a match.

The appropriate molecular tag is prepared as a dilute solution in, for example, ethanol. The solution is then applied (by spraying, dousing, washing, etc.) onto the surface of the vegetation or product at an early stage (such as a plant still growing on the farm). At any point thereafter officials can desorb the tag, such as with the use of water or an organic solvent such as ethanol or methanol, or mixtures of water and an organic solvent. The resulting solution is mixed with the corresponding antibody. The antibody will activate upon binding to the molecular tag and give off some sort of indication, such as changing the color of the solution. For example, the compound carbamazepine is widely commercially available and reacts to its corresponding antibody by changing the solution from colored to clear. This is an example of the quick field-based test.

Figure 2:
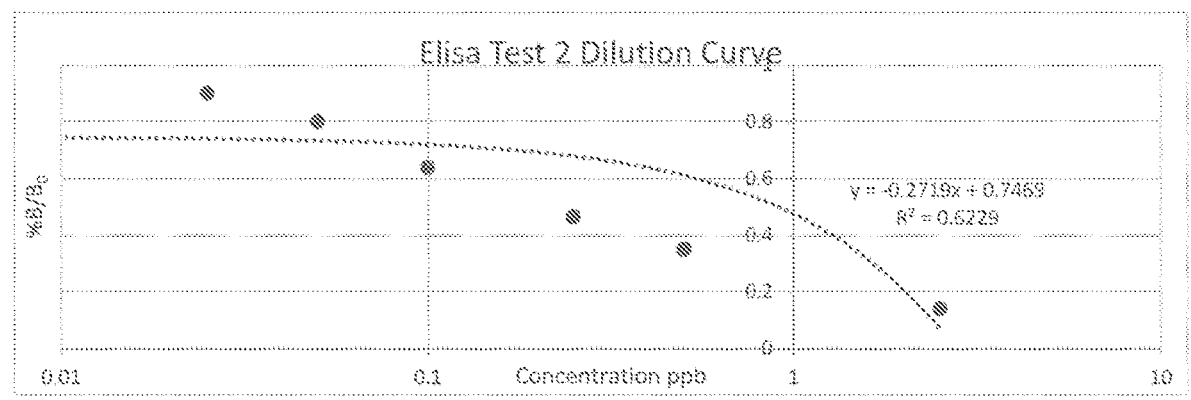
FIG. 2: Calibration curve created by serial dilution of a standard carbamazepine solution that can be used to quantify the amount of carbamazepine present in the hemp wash solution.

To ensure accuracy, the absorption characteristics (absorption spectra) of the resulting solution can be measured using ultraviolet-visible spectroscopy/spectrophotometry. For example, a portable UV-Vis spectrometer could be used on site. Additional embodiments of this technique may utilize attached software that rates the match of absorption spectra against standards. Sample analysis of industrial hemp amended with carbamazepine were tested using the antibody test resulting in the loss of color from the solution (FIG. 1). In addition a sample calibration curve demonstrates a decrease in absorbance with increasing carbamazepine (FIG. 2). For solutions that generate a colored solution, unique compounds will produce unique absorption spectra over a wide range of wavelengths. With absorption intensity varying by wavelength, relative positions (wavelength) of absorption maxima and minima can be used as tool for a qualitative match. Furthermore, for solutions that go from colored to clear a UV-Vis spectrometer will be more sensitive at picking up the presence of color than the human eye.

For the greatest depth of analysis, a laboratory-based analysis of samples can be used as a confirmation process for the positive identification of the presence of the molecular tag using mass spectrometry. This allows for the use of molecular tags that are further differentiated by being isotope labeled. "Isotope labeled," as used herein, means that the samples contain stable isotopes in ratios that differ from the naturally occurring ratios. This protects against counterfeiting. This is possible because isotope labeled compounds are chemically identical, but can be differentiated using mass spectrometry because they produce unique mass/charge signatures (mass spectra). Isotope labeled compounds can be custom produced. Furthermore, unique mixtures of differently labeled forms of the molecular tag can be used to further differentiate individual sources (producers) or for regional differentiation without requiring any changes to the field test. Essentially each producer could have their own unique mixture of different isotope labeled molecular tag (analogous to a unique bar code).

The following procedure was performed to detect a PYY peptide substrate with an antibody using paper to which an antibody is bound. Binding of the PYY peptide-anti-PYY peptide antibodies to the antibody bound to the paper generates an antibody complex that can be detected by a color indication.

Antibody Assay

All antibodies, enzymes, premixed BCIP/NBT solution, and trizma base used in this study were purchased form Sigma-Aldrich and used as received. HPLC grade MeOH from Fisher Chemical and Ultrapure water (18MΩ-cm) produced using a Barnstead NanoPure Infinity Ultrapure Water System were used in preparing solutions.

Antibody assay was performed by placing 20 µL of 0.05 µg/mL of anti-Rabbit IgG native antibody mouse monoclonal in a pH 7.4 tris buffer solution with 0.05% TWEEN 20 into 2 or more paper wells. This solution was allowed to dry on the paper. To the same wells 50 µL of 1% BSA (bovine serum albumin) solution in pH 7.4 tris buffer with 0.05% TWEEN 20 was spotted and allowed to dry for 30 minutes. The paper wells were them placed on blotting paper and washed with 250 µL of pH 7.4 tris buffer with 0.05% TWEEN 20 per well. This was followed by treating the wells with 0.1 µg/mL anti-PYY antibody produced in rabbit anti-Human and the wells are allowed to incubate at ambient temperature for 15 minutes. The wells were them placed on blotting paper and washed with 250 µL of pH 7.4 tris buffer with 0.05% TWEEN 20 per well and patted dry after the wash was wicked away, at this point the wells were ready for use. The wells were cut apart and labeled, to one was added a negative control which was just the tris buffer, to another was added a positive control containing biotinylated PYY, to the rest of the wells was added the samples. All the wells were allowed to incubate for 15 minutes at ambient temperature and were then washed with 250 µL tris buffer. The wells were then treated with 20 µL of 0.1 µg/mL streptavidin-Alkaline Phosphatase from *Streptomyces avidinii* in 7.4 pH tris buffer with 0.05% TWEEN 20 and allowed to incubate for 15 minutes. The wells were then washed with 250 µL of tris buffer and patted dry. The wells were finally treated with 20 µL of BCIP/NBT solution and pH 8.5 tris buffer and allowed to sit for 30 minutes. Any color change was observed and photographed.

ELISA assays are well known in biochemistry for their sensitivity and selectivity. In this example an ELISA assay was implemented using paper test pads, which help create a stabilized antibody complex that was used to detect a peptide biotinylated human-PYY that can be applied to plants and washed off later to identify the variety of plant material. FIG. 6 shows the process for how the test was performed. Prior to performing the test, the testing μ pads were prepared up to step 2. To these prepared μ pads was added the test solution, which was washed off of the plant material, and the solution was allowed to sit on the μ pad for 15 minutes. This step allowed for the peptide, if present, to bind to the antibody complex that was been built up on the surface of the paper. The next step, after washing the pad, was to treat the pads with streptavidin phosphatase, this is both an antibody that is selective for biotin and the enzyme that allowed the pad to be developed by adding a solution with dye precursors. With the addition of the BCIP/NBT solution, a color change was observed after a period of 30 minutes, this color change was the result of 5-bromo-4-chloro-3'-indolyphosphate being dephosphorylated and undergoing a dimerization reaction to give a variant of indigo, which precipitates onto the paper. Without presence of the biotinylated PYY there was no observable color change. The high sensitivity of this test is the fact that the final complex with the enzyme allows for the catalytic reaction with 5-bromo-4-chloro-3'-indolyphosphate, so with low signal more time will increase the response. For increased signal or to decrease the time required to develop the color change heat up to 40° C. can be applied.

Other peptides that can be used for this work include, but are not limited to: atrial natriuretic peptide human, vasoactive intestinal peptide fragment 1-12 human, Prepro-Atrial Natriuretic Peptide Fragment 26-55 human, Human NPPB, Tyr-C-Peptide human, Rat Leptin, Bovine IFNG, Bovine IL-17A, Canine IL-8, Equine Interleukin-10, Amyloid Precursor Protein α, Mouse CRG-2, Mouse Decorin, Mouse Eotaxin, Mouse Grem2, Mouse Spock3, Rat CNTF, Rat Robol, and custom peptides with non-natural amino acids which are readily available from Sigma-Aldrich. The corresponding antibodies for these peptides are used and are readily available from Sigma-Aldrich.

Example 2: Tagging of Industrial Hemp with Labeled Carbamazepine

To test the described approach for the field test, industrial hemp (<3% THC) was tagged with carbamazepine. The solvent (ethanol) was allowed to evaporate. The carbamazepine was desorbed in water and the carbamazepine in the resulting solution was positively identified when mixed with the antibody containing solution. Control hemp (no carbamazepine added) was tested in a similar process without a false positive being recorded.

Figure 3:
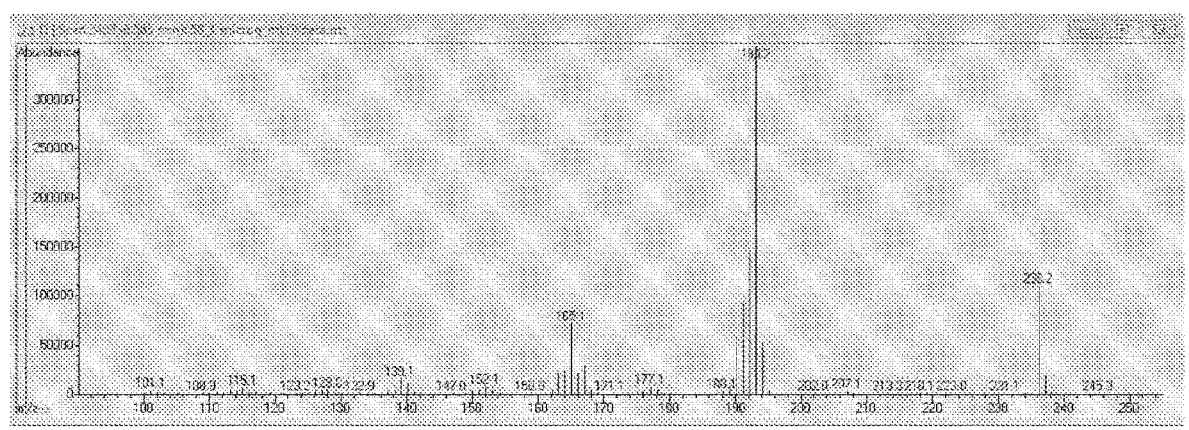
FIG. 3: Mass spectrum of unlabeled carbamazepine with the molecular ion at m/z=236 and fragments at m/z=193 and 165.

As a test of the laboratory-based confirmation industrial hemp was tagged with carbamazepine, which was then desorbed using ethanol. The extract was dried with sodium sulfate and analyzed for the presence of carbamazepine using GC/MS (FIG. 3). Carbamazepine was positively identified on replicate treated hemp samples and not detected on control samples.

Figure 4:
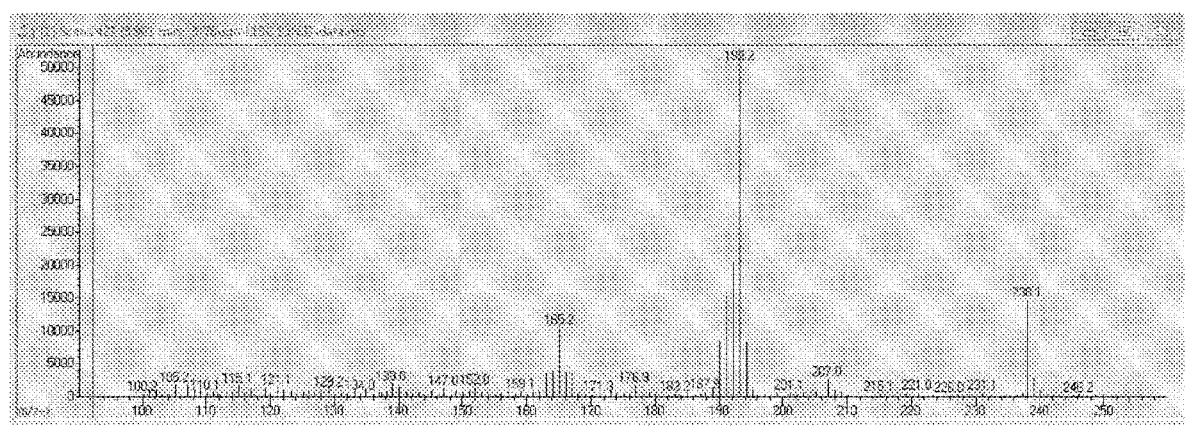
FIG. 4: Mass spectrum of isotope labeled carbamazepine ($^{13}C$, $^{15}N$) with the molecular ion at m/z=238 and fragments at m/z=193 and 165.
Figure 5:
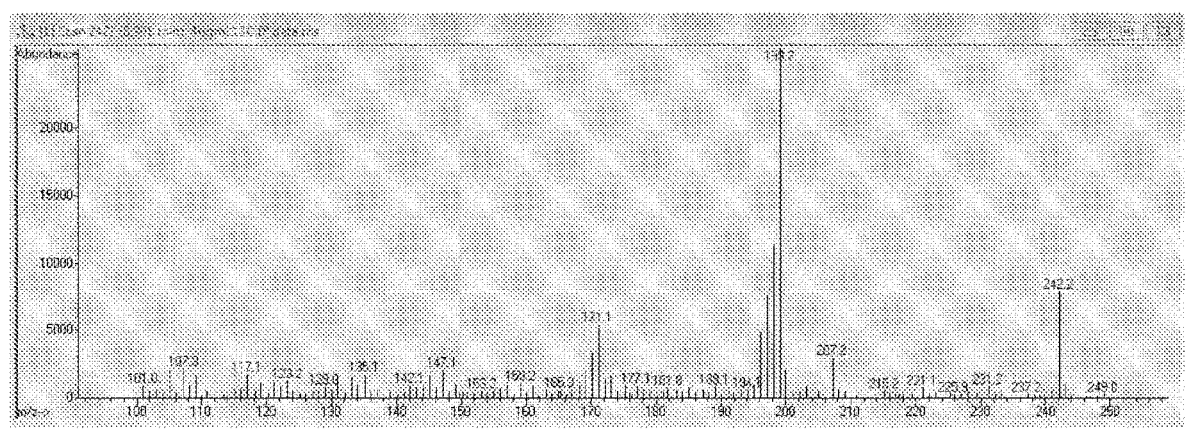
FIG. 5: Mass spectrum of isotope labeled carbamazepine ($^{13}C_6$) with the molecular ion at m/z=242 and fragments at m/z=199 and 171.
Figure 6:
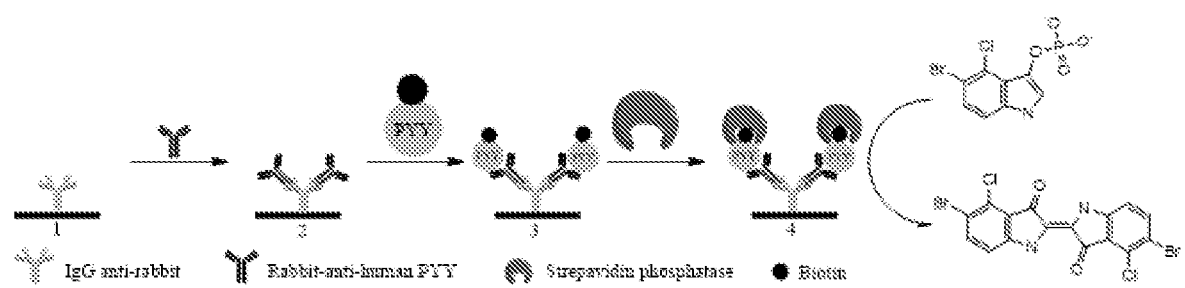
FIG. 6: Schematic representation of the process for building the antibody complex that allows for detection of biotinylated PYY peptide. The complex is built step-by-step, but steps 1 and 2 can be performed in advance to allow for more rapid testing.

As a demonstration of the ability to use isotope labeled or mixtures of an isotope labeled molecular tag four different isotope labeled carbamazepine samples were analyzed. These included $^{13}C_6$ (6 carbon 12 atoms replaced with carbon 13 atoms), $^{13}C$, $^{15}N$ (1 carbon 12 and 1 nitrogen 14 replaced with a carbon 13 and a nitrogen 15), $D_{10}$ (10 hydrogen atoms replaced with deuterium atoms), and $^{13}C_{15}$ (15 carbon 12 atoms replaced with carbon 13 atoms) forms of carbamazepine. These are four examples of available isotope labeled carbamazepine that could be mixed in different ratios with unlabeled carbamazepine to create unique five component mixtures that could be differentiated by mass spectrometry. As examples of the unique spectra produced by isotope labeled compounds sample mass spectra of the $^{13}C$, $^{15}N$ and $^{13}C_6$ labeled carbamazepine are shown (FIG. 4 and FIG. 5).

Although carbamazepine or another pharmaceutical could be the molecular tag used in large scale monitoring efforts, other possible molecular tags may include, but are not limited to, sugars, peptides, nucleic acids, and modified forms of these compounds. Isotope labeled forms of such compounds can be commercially produced as well as antibodies or nucleic acid probes for these potential molecular tags. As a result molecular tags can be rotated or changed on a regular basis without requiring a fundamental change in the technology.

Example 3: Tagging of Hemp with Unlabeled and Labeled Compounds

In this example an unlabeled substrate is applied directly to the hemp plant, and then desorbed with a solution of water and methanol. The solution containing the substrate is then placed on photopaper or a microfluidic paper-based analytical device (microPAD) that has been pretreated with an enzyme that reacts with the substrate to produce a color that is observable. Labeled substrates were also synthesized and used as summarized in Example 2, above, and described in greater detail below.

Synthesis

Chemicals: All chemicals were used as received without further purification. Solvents were of ACS reagent grade or better for all synthesis performed. All isotopically enriched chemicals used in synthesis were purchased from Cambridge Isotope Laboratories and used as received.

Syringaldazine was synthesized according to literature preparations (Bauer and Rupe, Anal. Chem. 43:421-425, 1971). An Erlenmeyer flask was charged with 0.4 mmol syringaldehyde which was dissolved in 1 mL of methanol. To this solution was added 4 mL of 0.1 M NaOH solution. This was allowed to stir for 30 minutes during which the solution turns yellow. After this, 1 mL of water with 0.2 mmol of hydrazine sulfate was added and allowed to stir for 3 hours. The product was filtered and recrystallized from hot ethanol. $^1H$ NMR (D6-DMSO) δ 9.10 (s, 2H), 8.59 (d, 2H), 7.16 (s, 4H), 3.83 (s, 12H).

Vanillin Azine was synthesized in an analogous way, to an Erlenmeyer flask was added 0.4 mmol vanillin and 1 mL of methanol. To this solution was added 4 mL of 0.1 M NaOH solution. This was allowed to stir for 30 minutes, resulting in a slightly yellow solution. To this solution was added 1 mL of water with 0.2 mmol hydrazine sulfate and stirred for 3 hours. The product was recrystallized from a minimal volume of hot ethanol. $^1H$ NMR (D6-DMSO) δ 9.72 (s, 1H), 8.58 (d, 2H), 7.46 (d, 2H), 7.25 (dd, 2H), 6.87 (d, 2H), 3.84 (s, 6H).

The synthesis of syringaldazine and vanillin azine is the result of a condensation reaction yielding the azine. For syringaldazine the product after recrystallization was 95% or better pure as shown in the NMR of this compound. Vanillin azine also shows high purity by NMR with a 95% or better purity by NMR after recrystalization. Isotopically labeled analogs of these compounds were synthesized in a similar manner using the appropriate $^{13}C$ and $^{15}N$ labeled starting materials. Other isotopically labeled versions of vanillin azine were also synthesized giving the same high purity, these compounds were the $^{13}C_{ring}$-vanillin azine, $^{13}C_{imine}$-vanillin azine, and $^{13}C_{imine}$-$^{15}N$-vanillin azine. The NMR spectra of these compounds showed splitting of the proton peaks where the $^{13}C$ was located due the decoupling pulse not being used.

Analytical Methods

HPLC grade MeOH from Fisher Chemical and Ultrapure water (18MO-cm) produced using a Barnstead NanoPure Infinity Ultrapure Water System were used in the sample preparation and tag removal process. Stock solutions of the vanillin, vanillin azine, and syringaldazine were prepared in HPLC grade MeOH. Separation of mixtures of varying ratios of unlabeled and isotopic labeled species were made by liquid chromatography on a Thermo Scientific Dionex UltiMate 3000. Detection of the analytes and isotopic ratios was accomplished using a Thermo Scientific TSQ Quantum Access Max triple quadrupole mass spectrometer. This instrument was controlled using Xcalibur 4.0 and TSQ series 2.6 SP1 software.

The separation of analytes was achieved using a Thermo Scientific Accucore aQ $C_{18}$ polar endcapped column (I.D. 100 mm×2.1 mm, 2.6 μm particle size). A binary gradient consisting of 0.1% formic acid in water (mobile phase A)

and 0.1% formic acid in methanol (mobile phase B) with a flow rate at 0.500 mL/minute. The solvent started at 15% mobile phase B and over 2.5 minutes mobile phase B was increased to 35%. From 2.5 minutes to 17 minutes mobile phase B was increased to 38% followed by an increase to 40% over the last minute. The ratios of unlabeled to isotopically labeled species were determined using mass spectrometer operated in the SRM mode measuring characteristic fragments generated in the collision cell (second quadrupole) and comparing the abundance of the ions produced from the parent molecules.

Paper Fluidics

Reagents for photoresist (D.E.R.™ 332, Proplene glycol monomethyl ether acetate, Triarylsulfonium hexafluorophosphate salts (mixed), PPS-[2-(3,4-Epoxycyclohexyl) ethyl]-heptaisobutyl substituted) were purchased from Sigma-Aldrich and used without further purification. The photopaper and photoresist were prepared in a similar method as in literature with slight changes (Cheng, et al., *Angew. Chemie—Int. Ed.* 49:4771-4774, 2010).

Photoresist solution was made by combining 134 mL of propylene glycol monomethyl ether acetate was added 31.66 g of D.E.R.™ 332 which was allowed to dissolve overnight. To this solution 9.3 g of PPS-[2-(3,4-epoxycyclohexyl) ethyl]-heptaisobutyl substituted was added and allowed to dissolve over night with stirring. The solution was activated with 20 mL of triarylsulfonium hexafluorophosphate mixed salts in propylene carbonate was added and allowed to mix for 2 hours. This solution was stored in a brown bottle covered in aluminum foil until use.

Photo-paper was prepared by spreading the photoresist evenly over the paper and allowed to soak into the paper. Each paper was placed into an oven at 100° C. unit the paper was dry to the touch (approximately 20-30 minutes) and stored in foil until ready to use. Patterning the paper was achieved by printing the positive (black where the resist is not wanted) of the desired pattern on an overhead transparency. The transparency was then placed on top of the photopaper and this was sandwiched between a board and a piece of glass and clamped down to keep everything in place. This was then placed in a UV light box for 15 minutes followed baking for 15 minutes at 100° C. and allowed to cool to room temperature. The paper was then washed with acetone (2×) and 70% isopropanol (2×) and hung up to dry at room temperature. The patterns were cut out to a size to be used.

Enzymatic Testing

Figure 7:
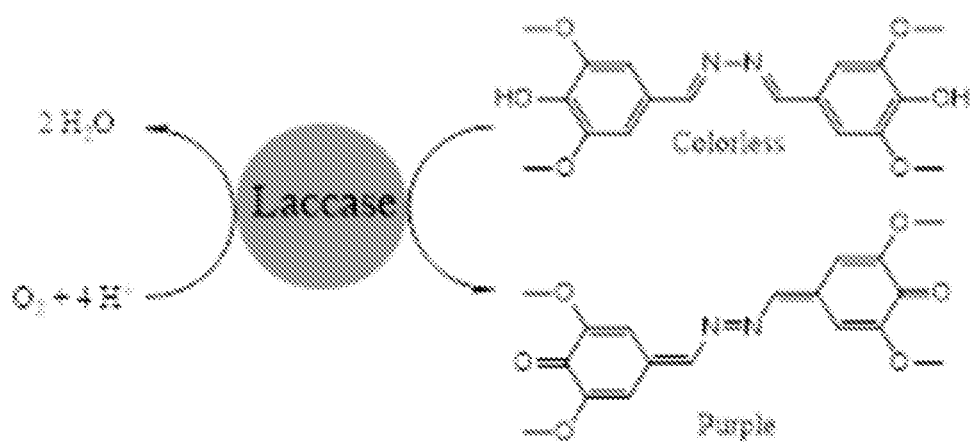
FIG. 7: Laccase mechanism for the formation of a colored compound through oxidation of syringaldazine (colorless) to tetramethoxy-azobismethylene quinone (TMAMQ—purple).

The laccase enzyme is a very selective enzyme for phenolic groups. This mechanism can be utilized for a color change that occurs as a method of applying a colorimetric tag to plant material, such as cannabis (FIG. 7). When both laccase and syringaldazine are both present with water the test solution will turn purple (Majcherczyk, et al., *Appl. Microbiol. Biotechnol.* 51:267-276, 1999; Hapiot, et al., *J. Electroanal. Chem.* 353:225-235, 1993). When syringaldazine is combined with vanillin and vanillin azine the same color change is observed. The presence of other phenolic compounds does not affect the color change of the syringaldazine. Vanillin azine, when tested alone with laccase, does not undergo a color change. This suggests that the second methoxy group is necessary for a color change to occur.

Enzymatic test was prepared by making a solution of 46.7 mg/mL of laccase from *Trametes versicolor* was prepared in 7.4 pH tris buffer with 0.05% TWEEN 20. To paper strip of at least 3 test spots, that were prepared as described above, was added 50 μL of laccase solution and the spots were allowed to stand and dry at room temperature. When the spots were dry they were ready for use. To this prepared test strip was added 20 μL of wash solution (1:1 methanol/water) to one spot (negative control), 20 μL of the wash solution (1:1 methanol/water) with 250 ppb syringaldazine to another spot (positive control), and the test solutions to the remaining spots. There were allowed to react for 15 minutes while the color develops. If no color developed in the positive control well, one drop of water was added to all wells to promote reaction with the enzyme.

The colorimetric tagging using syringaldazine was tested using tomato leaves because of the similar surface structure of the tomato leaf to cannabis leaves. One of the leaf samples was treated with syringaldazine solution of 50 ppm and all samples were allowed to dry until the leaves were stiff and cracked when pressure was applied to the leaf. The samples were then crushed to a course sample and washed with a 50:50 methanol:water solution and applied to the paper testing wells that were pretreated with laccase. The first well was treated with buffered water to verify that the laccase does not react with the paper itself to give a color change. The test strip was given 15 minutes of time to react and allow a color change to occur and only the sample treated with syringaldazine developed the purple color that is indicative of the syringaldazine reaction.

Other compounds that may be used in place of the syringaldazine include, but are not limited to: AzBTS-(NH$_4$)$_2$(2,2'-Azino-bis(3-ethylbenzothiazoline-6-sulfonic acid) diammonium salt) (Majcherczyk, et al., *Appl. Microbiol. Biotechnol.* 51:267-276, 1999), (1E,2E)-1,2-bis(benzo[d] oxazol-2-ylmethylene)hydrazine, diphenolazine, dihalodiphenolazine, 4-anisaldazine, cinnamaldazine, and salicylaldazine.

Other enzymes and substrate combinations can be used for colorimetric or fluorescent tagging as well. Replacing laccase with esterase the following substrates can be used and purchased from Sigma-Aldrich: 5-bromo-4-chloro-3-indolyl, fluorescein dilaurate, indoxyl acetate, 4-methylumbelliferyl acetate, 4-methylumbelliferyl butyrate, naphthol AS-D chloroacetate, 1-naphthyl butyrate, 4-nitrophenyl dodecanoate, 4-nitrophenyl myristate, 4-nitrophenyl octanoate, 8-octanoyloxypyrene-1,3,6-trisulfonic acid trisodium salt, resorufin acetate. Replacing laccase with lipase the following substrates could be used and are commercially available from Sigma-Aldrich: 4-methylumbelliferyl butyrate, 4-methylumbelliferyl butyrate, 4-methylumbelliferyl oleate, resorufin butyrate.

Isotopic Testing

Analysis of samples for isotopic testing was performed by initially separating each analyte by HPLC and utilizing an electrospray MS-MS by which the isotopic composition of each analyte was able to be analyzed. The analysis of the isotopic makeup of each analyte was done by comparing signal of one of the fragments listed in Table 1, which does not appear on another labeled compound present in the sample, and divided by the total signal for that fragment, the sum of the all possible signals for that fragment that are present in the sample (see the rows of FIG. 8 to find possible fragment masses that are related to the same fragment with different isotopic labeling) to give the ratio of the isotope. A list of fragments used in this study can be found in Table 1.

TABLE 1

| Compound Name | Mass (g/mol) | Precursor Ion | Fragment Ions | | | Collision Energy (V) |
|---|---|---|---|---|---|---|
| Vanillin | 152.15 | 153.060 | 153.06 | 125.1 | 93.2 | 10 |
| Vanillin Azine | 300.31 | 301.210 | 301.21 | 177.05 | 152.09 150.08 | 22 |
| $^{15}N$ | 302.30 | 303.110 | 303.11 | 179.06 | 153.07 151.05 | 22 |
| $^{13}C_{carbonyl}$ | 302.30 | 303.120 | 303.12 | 180.08 | 153.07 151.05 | 22 |
| $^{13}C_{ring}$ | 312.22 | 313.160 | 313.16 | 183.09 | 158.09 156.08 | 22 |
| Syringaldazine | 360.37 | 361.140 | 361.14 | 207.07 | 182.06 180.07 | 22 |
| $^{15}N$ | 362.35 | 363.130 | 363.13 | 209.07 | 183.08 181.07 | 22 |

Figure 9:
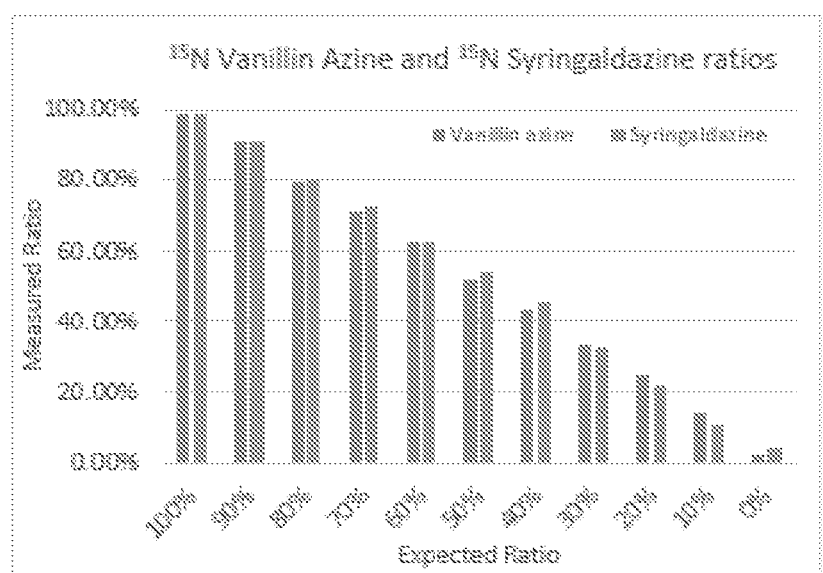
FIG. 9: Measured vs. expected values of vanillin azine and syringaldazine measured together in the same solution. Left bars—vanillin azine, right bars—syringaldazine.
Figure 10:
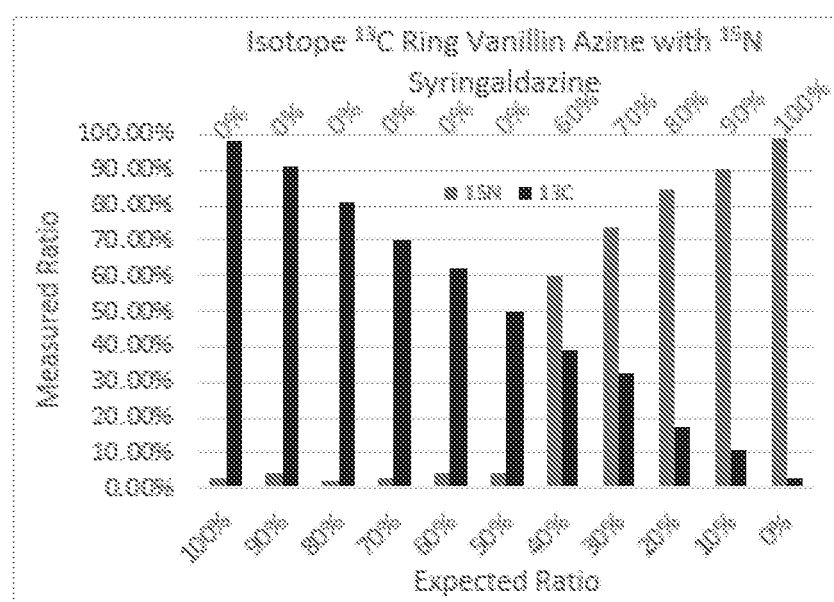
FIG. 10: Measured vs. expected values of $^{13}C_{ring}$-vanillin azine (right bars) and $^{15}N$-syringaldazine (left bars) measured together in the same solution.

The ratios for the fragments, with high enough abundance and did not overlap with other isotopic variations, were averaged together to improve the accuracy of the value obtained for each isotopic label. FIG. 9 shows the resulting percentages for $^{15}N$ on both the vanillin azine and syringaldazine of this method are in good agreement with the expected values. The same trend is observed for $^{13}C_{imine}$-vanillin azine with ratios between 0 and 100% at 10% increments. These ratios of each label do not have to be on the same trend, as shown in FIG. 10, and can be very different with each label having its own trend.

The possible variation can be seen by looking at the possible isotopic variation in FIG. 8, which shows 8 different isotopic variations for each of the azines and 3 for the vanillin. This gives a total of 19 different isotopes that can be used for the ratios to give a great amount of diversity to the number of combinations of these isotopes. Two or more different isotopically labeled species can be combined to give a larger amount of variations. Using just two isotopes varying between compounds gives more than 3400 different combinations using 10% increments in the ratios, increasing this to 3 isotopes with the same increment gives more than 2800 different combinations. If all possible isotopes on all three compounds, a portion of which is listed in FIG. 8, using the same 10% increments on the ratios there are more than 11000 combinations treating each compound isolated from each other, and if the relative concentration of the compounds with each other are also used there are more than $4.8 \times 10^{10}$ combinations possible.

Additional compounds can also be used as alternatively isotope labeled compounds for this type of application. A list of these possible compounds includes, but is not limited to: salicylaldazine, mint, limonene, cyclodextrin, starches, salicylaldehyde, cinnamaldehyde, 4-anisaldehyde, cinnamaldazine, 4-anisaldazine, butanedione, pentyl ethanoate, octyl ethanoate, methyl butanoate, ethyl butanoate, pentyl pentanoate, isobutyl methanoate, pentyl propanoate, citric acid, and many others.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more."

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

While the disclosure has been described in connection with specific embodiments thereof, it will be understood that the present disclosure is capable of further modifications by one of skill in the art. It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. The present disclosure is therefore intended to encompass any variations, uses, or adaptations of the invention following, in general, the principles of the invention and including such departures from the present disclosure as come within known or customary practice within the art to which the invention pertains and as may be applied to the essential features herein before set forth.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications, patents, and patent publications cited are incorporated by reference herein in their entirety for all purposes.

What is claimed is:

1. A method for identifying the source of a plant or part thereof, comprising:
   a) contacting the plant or a part thereof with a first compound indicative of the source of the plant and capable of being detected by a field-based assay; and
   b) identifying the plant or a part thereof by detecting the first compound or the absorption characteristics of the first compound, wherein the first compound is adhered to the surface of the plant or part thereof, wherein the first compound is desorbed using water or an organic solvent, and wherein the first compound comprises at least a first stable isotope label at a first location in the first compound, and the source of the plant or part thereof is identified by detecting the location of the first stable isotope label in the first compound.

2. The method of claim 1, further comprising contacting a plurality of plants or parts thereof with said first compound and at least a second compound, wherein the first compound is distinguishable from the second compound using said field-based assay.

3. The method of claim 2, wherein the first and second compounds comprise at least a first stable isotope label at a first location and wherein the first compound is distinguishable from the second compound using said field-based assay.

4. The method of claim 3, further comprising contacting the plurality of plants with a plurality of isotopic labeled variants of said first compound or said second compound comprising stable isotope labels in different locations or different isotope labels, wherein the variants are capable of serving as an indicator of source.

5. The method of claim 1, wherein the first compound is carbamazepine, vanillin azine, vanillin, syringaldazine, or a combination thereof.

6. The method of claim 1, wherein the first compound is a protein or peptide.

7. The method of claim 6, wherein the peptide is PYY.

8. The method of claim 1, wherein the first compound is a sugar or a polysaccharide.

9. The method of claim 1, wherein the first compound is a nucleic acid molecule.

10. The method of claim 1, wherein the field-based assay is an immunological assay.

11. The method of claim 1, wherein the field-based assay is an enzyme assay.

12. The method of claim 11, wherein the enzyme assay produces a color change or a change in fluorescence.

13. The method of claim 1, wherein the field-based assay is a nucleic acid binding assay.

14. The method of claim 1, wherein the first stable isotope label is independently selected from the group consisting of $^2H$, $^{13}C$, $^{15}N$, $^{17}O$, $^{18}O$, $^{33}S$, $^{34}S$, $^{36}S$ or $^{37}Cl$.

15. The method of claim 4, wherein said variants comprise a first and second different stable isotope label or a single stable isotope label at a plurality of locations in the first or second compound.

16. The method of claim 15, wherein the location or quantity of the first stable isotope label and the second stable isotope label in the first or second compound is identified by a laboratory-based assay.

17. The method of claim 16, wherein the laboratory-based assay is mass spectrometry.

18. The method of claim 1, wherein the field-based assay utilizes a microfluidic paper-based analytical device.

19. The method of claim 1, wherein the plant or part thereof is identified by a field-based assay and a laboratory-based assay.

20. The method of claim 1, wherein at least a portion of the first compound is removed from the plant or part thereof before the identifying step.

21. The method of claim 1, wherein the plant part is a cell, a seed, a root, a stem, a leaf, a head, a flower, or pollen.

22. The method of claim 1, wherein the first compound is indicative of the intended use of or the producer of the plant or part thereof.

23. The method of claim 15, wherein the location of the first stable isotope label and the second stable isotope label in the first or second compound, the quantity of stable isotope labels in the first or second compound, or the variants of isotope labeled forms of the first or second compound is indicative of the origin of the plant or part thereof.

24. A method of distinguishing a first plant or part thereof from a second plant or part thereof, comprising:
   a) obtaining a plant or part thereof that has been contacted with:
      (i) a first compound capable of being detected by a field-based assay, the first compound comprising a first stable isotope label at a first location in the first compound and a second stable isotope label at a second location in the first compound, or
      (ii) a second compound capable of being detected by a field-based assay, the second compound comprising a third stable isotope label at a first location in the second compound and a fourth stable isotope label at a second location in the second compound; and
   b) detecting in a sample of the plant or part thereof the first compound, the absorption characteristics of the first compound, or the location of the first stable isotope label and the second stable isotope label in the first compound, or the absorption characteristics of the second compound, or the location of the third stable isotope label and the fourth stable isotope label in the second compound, wherein the presence of the first compound is indicative of the sample comprising the first plant or part thereof and the presence of the second compound is indicative of the sample comprising the second plant or part thereof,
   wherein the first compound or the second compound is adhered to the surface of the plant or part thereof, and wherein the first compound or the second compound is desorbed using water or an organic solvent.

25. The method of claim 24, wherein the first compound comprises a first stable isotope label at a first location in the first compound and a second stable isotope label at a second location in the first compound, and the second compound comprises a third stable isotope label at a first location in the second compound and a fourth stable isotope label at a second location in the second compound, and detecting the location of the first stable isotope label and the second stable isotope label in the first compound or the location of the third stable isotope label and the fourth stable isotope label in the second compound, wherein the presence of the first compound is indicative of the sample comprising the first plant or part thereof and the presence of the second compound is indicative of the sample comprising the second plant or part thereof.

26. The method of claim 24, wherein the first compound is carbamazepine, vanillin azine, vanillin, or syringaldazine.

27. The method of claim 25, wherein the first compound is carbamazepine, vanillin azine, vanillin, or syringaldazine comprising a first stable isotope label at a first position and a second stable isotope label at a second position, and the second compound is carbamazepine, vanillin azine, vanillin, or syringaldazine comprising the first stable isotope label at a third position and the second stable isotope label at a fourth position.

28. The method of claim 24, wherein the first plant is medical cannabis and the second plant is recreational cannabis.

29. The method of claim 24, wherein the first plant is an organic product and the second plant is a non-organic product.

30. The method of claim 24, wherein the first plant is from a first location and the second plant is from a second location.

31. The method of claim 24, wherein the first plant is from a first grower and the second plant is from a second grower.

32. The method of claim 24, wherein at least a portion of the first compound or the second compound is removed from the plant or part thereof before the identifying step.

* * * * *